United States Patent
Meyer et al.

(10) Patent No.: US 9,034,260 B2
(45) Date of Patent: May 19, 2015

(54) APPARATUS AND METHOD FOR SELECTING PARTICLES

(75) Inventors: Heiko Meyer, Hannover (DE); Raoul Amadeus Lorbeer, Hannover (DE); Alexander Heisterkamp, Isenhaga (DE); Detlef Rath, Neustadt (DE)

(73) Assignee: MASTERRIND, GmbH, Verden (DE)

( * ) Notice: Subject to any disclaimer, the term of this patent is extended or adjusted under 35 U.S.C. 154(b) by 0 days.

(21) Appl. No.: 13/379,944

(22) PCT Filed: Jun. 24, 2010

(86) PCT No.: PCT/EP2010/058995
§ 371 (c)(1),
(2), (4) Date: May 10, 2012

(87) PCT Pub. No.: WO2010/149739
PCT Pub. Date: Dec. 29, 2010

(65) Prior Publication Data
US 2012/0225418 A1    Sep. 6, 2012

(30) Foreign Application Priority Data
Jun. 24, 2009   (EP) .................................... 09163691

(51) Int. Cl.
G01N 33/00 (2006.01)
B41J 2/135 (2006.01)
B41J 2/02 (2006.01)
G01N 15/14 (2006.01)

(52) U.S. Cl.
CPC ...... G01N 15/1459 (2013.01); *G01N 2015/149* (2013.01)

(58) Field of Classification Search
USPC .............................................. 422/73
See application file for complete search history.

(56) References Cited

U.S. PATENT DOCUMENTS

| | | | |
|---|---|---|---|
| 5,135,759 A | 8/1992 | Johnson | |
| 5,158,889 A * | 10/1992 | Hirako et al. | 435/286.3 |
| 2004/0114380 A1 * | 6/2004 | Schmitt et al. | 362/464 |
| 2004/0190567 A1 * | 9/2004 | Lutgen et al. | 372/25 |
| 2004/0243111 A1 * | 12/2004 | Bendett et al. | 606/5 |
| 2005/0112541 A1 * | 5/2005 | Durack et al. | 435/2 |
| 2005/0249636 A1 | 11/2005 | Tacklind et al. | |
| 2007/0117086 A1 * | 5/2007 | Evans et al. | 435/4 |
| 2008/0261295 A1 | 10/2008 | Butler et al. | |

FOREIGN PATENT DOCUMENTS

| | | |
|---|---|---|
| JP | 60 251872 | 12/1985 |
| WO | WO 2004/012133 | 2/2004 |

OTHER PUBLICATIONS

Database EPODOC, XP002561514, European Patent Office, The Hague, NL Dec. 12, 1985.

* cited by examiner

*Primary Examiner* — Jill Warden
*Assistant Examiner* — Brittany Fisher
(74) *Attorney, Agent, or Firm* — Greer, Burns & Crain, Ltd.

(57) ABSTRACT

The invention provides a device and a method for flow cytometric fractionation of particles contained in a fluid stream, wherein sections of the fluid stream, especially droplets if the fluid stream is a droplet stream, are irradiated with a laser. The laser disposed for the irradiation of the sections of the fluid stream can have a wavelength which is absorbed by the fluid and can have a sufficient radiation duration and radiation intensity to deflect sections of the fluid stream.

19 Claims, 7 Drawing Sheets

APPARATUS AND METHOD FOR SELECTING PARTICLES

Figure 1:
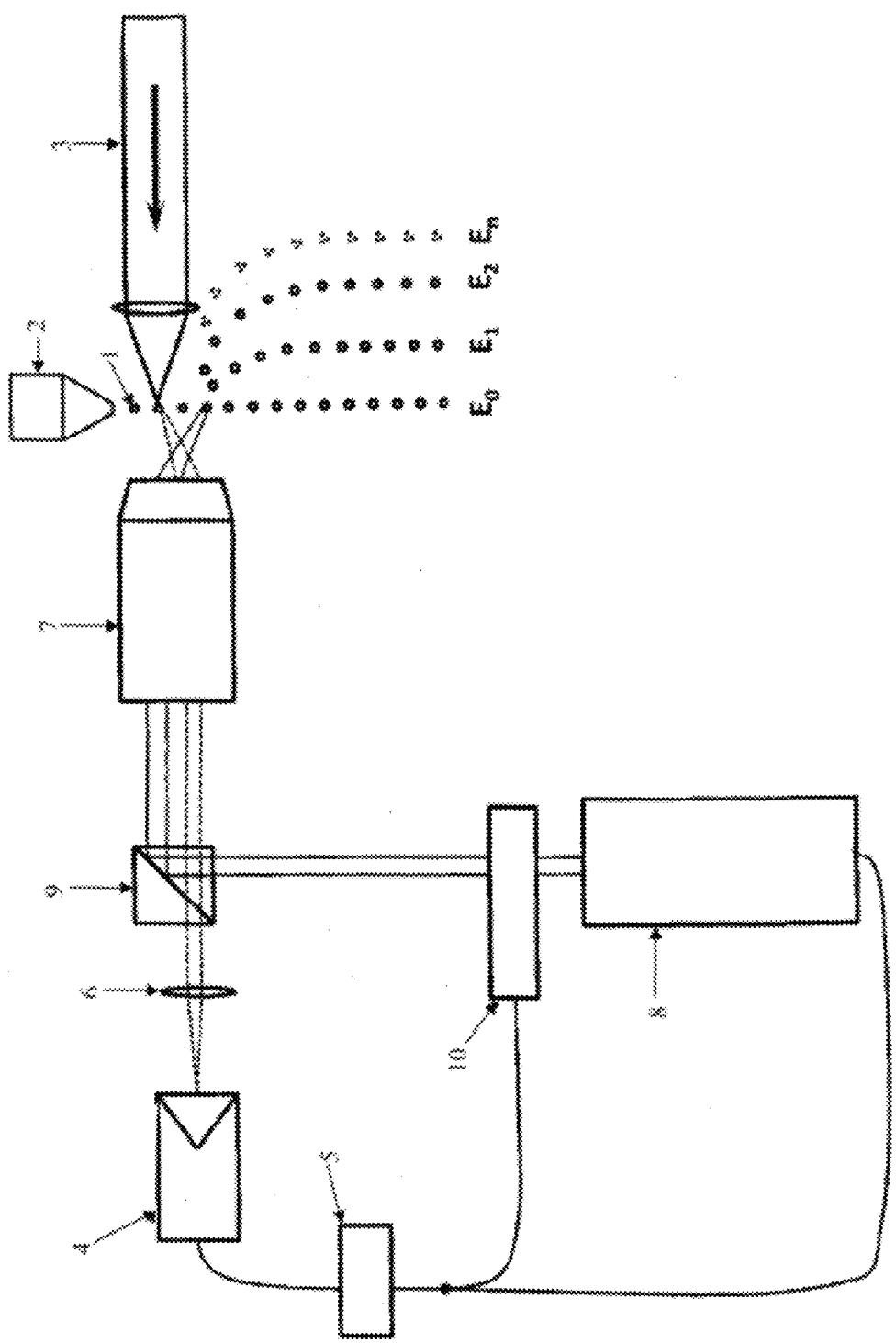

The invention relates to a device and a method for the selection of particles, especially for flow cytometric fractionation and sorting of individual particles contained in a fluid stream, respectively, by deflection of sections of the fluid stream by means of a laser directed onto the fluid stream. Accordingly, the invention also relates to the use of the device as a sorting means for particles. Optionally, in addition to the deflection of sections of the fluid stream the particles contained therein can be inactivated by specific heating by means of a laser directed onto the fluid stream. The deflection and/or the heating occurs by controlling and triggering of the laser or of the two or more lasers, respectively, in dependence from a detected signal which is specific for at least one particle or for its labelling. The method realizes the selection of particles, especially when these are biological cells, by fractionation and optionally by additional heating of individualized particles. According to the invention, particles are guided past a detector, wherein the particles preferably are contained in a fluid stream and preferably are singled in the fluid stream. The fluid can be gaseous or liquid and preferably is a continuous liquid stream or a stream of liquid droplets which particularly preferred contain at maximum one particle each. Preferably, the fluid is an essentially aqueous composition. Accordingly, the device preferably is disposed for generating a fluid stream of liquid droplets and for that preferably has a nozzle subjected to ultrasound from which the fluid stream emerges or an ultrasonic head arranged in the flow channel of the nozzle. The detected signal for example is an optical signal which especially is detected at a wavelength emitted by a dye or by dye conjugate specific for the particle after irradiation by an excitation wavelength. The generation of the fluid stream containing the particles, the detection of at least one property of the particles contained in the fluid stream and the generation of a control signal from the detection signal with subsequent control of a selection means, e.g. of a fractionation means and sorting means, respectively, for sorting and fractionation of the particles, respectively, in correspondence to the detection signal can occur by known devices and methods. The invention provides a method and a device having a selection means allowing sections of the fluid stream, preferably sections of the fluid stream containing particles, without applying a charge onto the fluid stream and without deflection of the fluid stream in the electric field. In this way, the invention avoids the impact of voltage on particles during their selection, e.g. by fractionation by means of deflection into two or more fractions.

STATE OF THE ART

U.S. Pat. No. 5,135,759 describes a FACS device for sex-chromosome specific sorting of spermatozoa which are singled in a fluid stream and which are sorted corresponding to the signal of a DNA specific fluorescence dye (Hoechst bisbenzimide H 33342). For a precise measurement the device of U.S. Pat. No. 5,135,759 in addition to the detector for measurement of a signal characteristic for the desired particle property contains a further detector which is arranged at an angle to the aforementioned detector and which receives a fluorescence signal of the particles characteristic for the orientation of the particles in the fluid stream. The control signal for the sorting means is generated based on the signal specific for the DNA content of the spermatozoa and on the signal characteristic for the orientation of the spermatozoa in the fluid stream. The fractionation occurs by applying a voltage to the fluid stream in order to electrically charge its sections and the droplets produced therefrom, respectively, in correspondence to the signal detected, such that upon the subsequent passage of an electric field they are electrostatically deflected and are collected in separate fractions.

WO 2004/012133 A2 describes the alignment of cells in a liquid stream guided in a channel by irradiation of the liquid stream with a multitude of laser beams forming a holographic optical trap.

U.S. Pat. No. 5,158,889 describes the inactivation of cells by a second laser beam which cells were irradiated in a liquid stream by a first laser beam and were identified by a detector. In this method, the second laser beam has a wavelength which passes through the liquid and is not absorbed by the liquid, respectively, in order to heat the particle directly at the required velocity during its movement through the second laser beam.

US 2008/0261295 A1 describes the deflection of cells streaming in the core stream within a sheath liquid in a channel by means of an optical switch. The optical switch is formed by a laser beam controlled on the basis of a fluorescence signal detected for the cells. For an impact on the cells and on the liquid in the direct vicinity of the cells, respectively, the laser beam has to have a wavelength which is not absorbed by the liquid.

The English language abstract of JP 60251872 A describes a copper-vapour laser for irradiation of cells in a sheath stream and the detection of the scattered light or fluorescence light by a detector. For sorting, a droplet stream is subsequently produced from the sheath stream and the cells are electrically charged and deflected in an electric field.

US 2005/249636 A1 describes the deflection of cells streaming in a channel within a liquid into a branching channel in that in another branching channel a vapour bubble is produced, e.g. by means of laser irradiation.

OBJECT OF THE INVENTION

In view of known devices and methods it is the object of the invention to provide an alternative method and an alternative device for flow cytometric fractionation of particles in a fluid stream corresponding to a signal specifically detected for the particles and their marker, respectively, and therein to avoid the impact of strong electric fields on the particles.

GENERAL DESCRIPTION OF THE INVENTION

During the preparations of the invention it has been found that by the flow cytometric fractionation of animal cells, especially of spermatozoa, damages are caused to the cells. Such cell damages in particular are alterations of the structures of the mitochondria in the middle part of the sperm tail leading to a reduced motility, especially upon incubations at room temperature or upon storing and to the reduction of the life span, and especially to a reduced fertilizing capability. Presently it is assumed that these impairments of cells by flow cytometric sorting methods, for example according to U.S. Pat. No. 5,135,759, is attributed to the voltage affecting the cells and to the electric field, respectively, which are applied for separation of droplets from the droplet stream. This is because the voltages applied therein are in a dimension that is also used for the electroporation of animal cells, such that corresponding depolarizations of the cell membrane can occur. If cells pass through an electric field, as e.g. in the deflection step of the method of U.S. Pat. No. 5,135,759, in addition membrane damaging oxygen radicals are generated frequently.

During the preparation of the present invention, analyses of spermatozoa which have passed through an electric field according to the method of U.S. Pat. No. 5,135,759 have shown that solely the electric field causes alterations of the sperm middle part. Such, electron-microscopic pictures of spermatozoa which in the sorting method have passed through such an electric field show structural alterations of the cell wall, partly even tearings, and structural alterations of the sperm middle part and in particular altered mitochondria as damages, e.g. expanded christae of mitochondria. Such alterations were not observed, if the sperms passed through the same sorting method, but without applying voltage to the plates which generate the electric field between one another for deflection of charged particles.

The invention achieves the object by the features of the claims, and especially provides a device and a method for flow cytometric fractionation of particles contained in a fluid stream, wherein sections of the fluid stream, especially droplets in the case the fluid stream is a droplet stream of liquid droplets, are irradiated with a laser. According to the invention, the laser beam is directed onto the fluid stream and has a wavelength such that liquid is heated essentially only superficially and thereby evaporates superficially such that the superficially irradiated section of the fluid stream is accelerated and deflected into the direction opposite the laser beam, respectively. For the production of preparations of sorted particles, the particles deflected by the laser beam or the particles not deflected from their flow path by the laser beam can be collected.

The laser that is disposed for the irradiation of the sections of the fluid stream and is directed onto the fluid stream in a first embodiment can have a wavelength and can be disposed for generation of radiation having a wavelength which is absorbed by the fluid and which has a sufficient radiation duration and radiation intensity, respectively, to heat a portion of the fluid which preferably is only a superficial portion of the fluid. If the fluid is a liquid, the laser radiation acting onto a section of the liquid stream applies a total energy onto the irradiated superficial section of the liquid stream which causes a superficial portion of the liquid to evaporate. By the laser-induced local superficial evaporation the section of the liquid stream irradiated by the laser radiation is accelerated into the direction opposite to the laser radiation. This acceleration generated by the essentially only superficial laser irradiation imparts a different direction of movement and a different flight path, respectively, to this section of the fluid stream than to the non-irradiated fluid stream. The laser-irradiated section of the fluid stream therefore can be collected in a collecting receptacle which is arranged at a distance to the flight path assumed by the non-irradiated liquid stream.

In a second embodiment the laser is directed onto the fluid stream and focused on the surface of the fluid for superficial heating of the fluid. Therein, the laser can be disposed for generation of radiation having a wavelength which is absorbed by the fluid as it is the case in the first embodiment, or having a wavelength which without focusing on the surface could pass through the fluid. In this embodiment, the laser is equally disposed for superficial heating of the fluid, wherein the focusing onto the surface induces a photodisruption at the fluid surface by nonlinear multiphoton absorption. Preferably, the focusing of the laser onto the surface of the fluid stream occurs by means of optical elements having in total a numerical aperture of 0.2 to 1.4, preferably having a numerical aperture of 0.3 to 1.0, especially preferred of 0.4 to 0.8. The optical elements which in their arrangement have such a numerical aperture and which are arranged in the beam path of the sorting laser, can be objectives, einzel-lenses, a lens combination, mirrors, concave mirrors, parabolic mirrors and/or mirror combinations.

In these embodiments the selection unit can also be termed a sorting unit, and the laser directed onto the fluid stream which only superficially heats the fluid sectionally to the superficial evaporation of the fluid, can be termed a sorting laser. This is because the sorting laser is disposed for superficially irradiating the fluid in its sections for which the sorting laser on the basis of a signal of a detector is tripped and triggered, respectively, such that the sections of the fluid stream which are superficially irradiated are deflected and collected in a collecting receptacle which is arranged separately from a collecting receptacle arranged in the flow path of the non-deflected fluid sections. Therein, the detector is disposed to generate a signal in dependence from a predetermined measured value, e.g. at preset fluorescence intensity of a dye contacted with the particles.

In a further development of the invention in which an additional laser is disposed as a heating unit, the device in addition to the sorting laser, which is disposed for the essentially exclusively superficial heating of the fluid, has a laser which is disposed to irradiate the fluid sectionally in dependence from a signal of the detector at a wavelength which is not absorbed by the fluid, but for which the fluid is essentially optically transparent, such that the laser radiation can have an effect on the particle contained in the section of the fluid stream. Therein, an influence on the particles occurs by the particles within the fluid stream being heated in a targeted manner, e.g. up to thermal inactivation. Especially in embodiments of the method in which particles are biological cells, especially animal cells, particularly preferred spermatozoa, the biological activity of the cell is altered by the heating, in particular the cells are inactivated in a targeted manner by heating. Therefore, for the purposes of the invention, the term of fractionation or sorting also comprises the targeted inactivation of at least a portion of the particles in the alternative to or in addition to the deflection, and collecting of the particles treated by means of laser radiation, e.g. in admixture with the particles not heated by laser radiation in a targeted manner, and/or upon deflection of particles by means of a sorting laser in a fraction of the deflected particles. In these embodiments a separation of the particles altered by means of laser irradiation, especially of inactivated cells from the non-inactivated cells, is not necessary, but is possible by combination with a sorting laser, since the inactivated cells no longer have a biological activity, for example in the case of spermatozoa a portion of which is inactivated, especially a sex-chromosome specific portion is inactivated.

The device according to the invention generally has a nozzle for generation of a fluid stream containing particles and preferably has a pump or a connected pressure source. At a distance to the outlet opening of the nozzle an irradiation means is arranged, the radiation of which is directed onto the fluid stream emerging from the nozzle, and opposite from the irradiation means or at an angle thereto a detector is arranged, the sensor surface of which is directed onto the fluid stream. The detector preferably is an optical detector the sensor surface of which preferably is provided with an optical element transparent for preselected wavelengths which eliminates radiation of other wavelengths. In this manner, the detector can be preset to a preselected wavelength, preferably to the wavelength which is emitted by a dye specific for the particle and by a dye or a dye conjugate associated with the particle, respectively. For excitation of the emission of radiation from a dye or dye conjugate with which the particle is contacted, the radiation means preferably is disposed for emitting an excitation wavelength.

The detector is connected to a control unit which receives the measuring signals emitted by the detector and which is disposed for generating control signals for a selection unit on the basis of these measuring signals and to transmit the control signals to the selection unit. Generally, a means for generation of a fluid stream containing particles having a nozzle from which the fluid stream exits, an irradiation means arranged at a distance to the nozzle and a detector assigned to the irradiation means, the detector being connected to a control unit, can correspond to the functionally equivalent means of a FACS device, especially to a FACS device corresponding to U.S. Pat. No. 5,135,759, the disclosure of which is incorporated into the description by reference.

The device according to the invention has a selection unit comprising a laser which is also denoted as a selection laser or sorting laser, the beam path of which is directed onto the fluid stream, preferably onto a section of the fluid stream arranged in a second position at a greater distance to the nozzle than the first position, in which that section of the fluid stream is arranged onto which the radiation of the irradiation means is directed. In this manner, the laser of the selection unit is arranged such that its beam path is directed onto a section of the fluid stream of a second position which is arranged in the flow path of the fluid and in the flight path of droplets from the fluid, respectively, downstream of the first position of the section of the fluid stream at which the irradiation means for detection is directed onto the fluid stream and in which the detection occurs. In this manner, a section of the fluid stream is firstly detected in a first position by irradiation and detection of a signal specific for a particle, and at a temporal distance is submitted to the fractionation by deflection of a section by means of an essentially exclusively superficial irradiation of the sorting laser in a second position arranged downstream. For coordination of the radiation of the sorting laser for the irradiation of the second position of the same section of the fluid stream for which a measuring signal was detected in a first position and which in the temporal distance of the fluid stream contains the same particle, the control unit preferably has a delaying unit which temporally delays control signals for the controlling of the sorting laser by a predetermined amount.

For controlling the laser radiation emitted by the sorting laser, its laser medium itself can be controlled by a control unit, especially for generation of laser beam pulses in dependence from control signals. Preferably, the sorting laser is a continuous (CW) laser, especially a solid-state laser or $CO_2$-laser, in the beam path of which no or optionally at least one optical element connected to the control unit and controlled thereby is arranged, for example an optical switch, the transmission of which is controlled by the control unit. Preferred laser beam pulses have energies in the range from 1 to 10 µJ, e.g. 1.8 to 5 µJ, especially 3.5 µJ, since e.g. the irradiation with a pulse energy of 1.8 µJ achieves a deflection of water droplets by 100 µm/cm (1.5 mm at a falling distance of 15 cm), and at a pulse energy of 3.5 µJ a deflection of water droplets by 200 µm/cm (3 mm at a falling distance of 15 cm). Preferably, the laser beam pulses have pulse durations ($t_p$) of from $1\times10^{-4}$ to $1\times10^{-15}$ s. Preferably, pulsed lasers have repetition rates (pulse repetition rates) of from 1 Hz to 200 MHz. A pulsed laser can have a connected triggering means or can be formed by a CW laser in the beam path of which an optical switch is arranged which is controlled by a connected triggering means, or can be formed by a pulsed laser in the beam path of which a pulse picker is arranged which selects individual pulses from a pulse group in a triggered manner and guides them into a beam path having optical elements which direct the selected pulses onto the fluid stream.

Particularly preferred, in the beam path of the sorting laser there is arranged a focusing means, for example a microscope objective, which focuses the laser radiation of the sorting laser onto a section of the fluid stream. Particularly preferred, the detector is arranged in an optical path running through the focusing means that is arranged in the beam path of the sorting laser, wherein the beam path of the sorting laser is separated from that of the radiation directed to the detector by a spaced arrangement of these beam paths through the focusing means. Therein, the beam path directed out of the focusing means to the detector can be separated from the beam path of the sorting laser by a beam splitter which deflects the beam path from the sorting laser to the focusing means or the beam path from the focusing means to the detector, while the beam splitter is transparent for the respective other beam path.

Instead of the arrangement of the detector such that its beam path runs through the focusing means of the sorting laser, the irradiation means for excitation of the fluorescence of a dye or dye conjugate contacted with the particle can be arranged such that its excitation radiation is coupled into its focusing means at a distance to the beam path of the sorting laser. In this embodiment the detector preferably is arranged such that its sensor surface is arranged in a beam path which is located at an angle to the beam path of the irradiation means for fluorescence excitation.

The control unit is provided with a programme which in dependence from the intensity of a detection signal transmitted by the detector generates and transmits control signals to the sorting laser and/or to optical elements in its beam path which are suitable to direct the radiation of the sorting laser in dependence from the detection signal with temporal delay onto a spaced section of the fluid stream, e.g. in the second position at a distance downstream of the first position of the section of the fluid stream in which the detector has received emitted radiation and has generated a detection signal. By means of the arrangement of the section onto which the laser radiation of the sorting laser has an effect in a second position at a distance to and downstream of the section onto which the detector and/or an excitation radiation source is directed in the first position, that section of the fluid stream containing the detected particle can be irradiated with the radiation of the sorting laser due to a temporal delay of the laser irradiation for detection corresponding to the duration of the fluid movement between the first position and the second position.

In addition to a detector for measurement of a measuring signal the device can also have one or more second detectors which measure properties of particles and/or of the fluid. Preferably, the device has a second detector, optionally also a second excitation light source the radiation of which is directed onto the fluid stream, wherein the second detector particularly preferred receives a fluorescence signal for the particles and transmits it to the control unit from which the control unit identifies the relative orientation of the particles, especially of non-rotationally symmetrical particles like spermatozoa, and the control unit generates the control signal, also on the basis of this second detection signal in combination with the first detection signal of a detector.

In a special embodiment, in the beam path of the sorting laser there is a beam splitter arranged which divides or directs the optical path and the beam path of the sorting laser, respectively, into a first and a second partial path, each of which is directed onto the fluid stream. The first and second partial paths can be directed onto spaced sections of the fluid stream, for example onto sections of the flow path of the fluid and of the flight path of droplets for a fluid stream of liquid droplets, respectively. In this manner, the same section of the fluid stream can be irradiated by laser radiation along the first and/or second partial path at a temporal distance. Preferably, a first optical switch is arranged in the first partial path and a second optical switch is arranged in the second partial path, each of which switches is connected to a control unit and controlled thereby. For the alignment of at least one of the first and second partial paths onto the fluid stream, mirrors are arranged within these.

In addition the device apart from a first sorting laser can have one or more second sorting lasers the beam path of which is also directed onto the fluid stream, wherein second sorting lasers are disposed as is the first sorting laser and optionally emit the same or a different wavelength. In this manner, the precision of the sorting method can be increased if the first sorting laser emits radiation having a wavelength which is absorbed by the fluid and results in its sectional deflection, while the beam of a second sorting laser is directed at an angle to the beam of the first sorting laser. Preferably, the second or further sorting laser is also directed onto the fluid stream and has a wavelength absorbed by the fluid and/or is focused on the surface of the fluid, such that the laser radiation causes an only superficial heating and therefore a second or further deflection of the fluid. With a second sorting laser which generates radiation having a wavelength absorbable by the fluid, its section of the beam path directed onto the fluid stream is preferably arranged at an angle of from 30° to 180°, more preferred of from 60° to 90° to the section of the beam path of the first sorting laser directed onto the fluid stream. Optionally additionally, a further laser can be disposed for generation of radiation having a wavelength which essentially is not absorbed by the fluid and be directed onto the fluid stream in order to heat the particles in the irradiated section of the fluid stream.

Second sorting lasers and optional lasers emitting radiation not absorbed by the fluid can be connected to the control unit as is the first sorting laser and can be controlled by its control signals which are generated in dependence from detection signals of the detector. For embodiments in the selection unit of which one or more second sorting lasers are contained, it is preferred that these are directed onto a third and a further position of the fluid stream, respectively, each of which is spaced further from the nozzle than the second position in order to direct second sorting lasers onto the fluid stream further downstream independently from the first sorting laser. Optionally, the radiation of a sorting laser can be divided and/or deflected by optical elements and can be directed at a deviating angle and/or onto the fluid stream, optionally onto the site at which the same section of the fluid stream is localized at a temporal distance.

The description of the method according to the invention also applies as description of the disposition of the components of the device for carrying out the steps of the method mentioned; the description of the device according to the invention also refers to the steps of the method carried out therewith according to the described functioning of the components of the device. Accordingly, the device according to the invention is suitable for use in a method according to the invention. Preferably, the method relates to the sex-chromosome specific sorting or inactivation of non-human mammalian gametes, respectively, especially of non-human mammalian spermatozoa, especially of the bovine, the pig, the horse, the sheep, and the camel.

The method for sorting of particles according to the invention comprises the formation of a fluid stream containing particles, especially by pumping of the fluid, for example by means of a pump or by pressurization, e.g. by connection of an overpressure source, detecting of a property of the particles within the fluid stream and generating a detection signal for the detected property, generating a control signal according to the detection signal, preferably with a temporal delay of the control signal, controlling of a selection unit by the control signal, wherein the particles are sorted into at least two fractions by means of a selection unit, wherein the sorting comprises targeted laser irradiation to at least a section of the fluid stream and collecting the laser-irradiated section and/or the non-laser irradiated section of the fluid. Preferably, the fluid stream is generated by streaming of the fluid containing particles through a nozzle. Particularly preferred, the fluid stream is a stream of successive droplets of the fluid, also related to as a droplet stream, such that a fluid droplet is a section of the fluid stream in which preferably one particle each is contained. Further preferred, in the method non-human mammalian spermatozoa are utilized and selected as particles, especially after contacting with a DNA-specific dye or a sex-chromosome specific dye conjugate.

The collecting preferably occurs by receiving sections of the fluid stream in collecting receptacles arranged in the flow path and flight path of the non-laser irradiated fluid stream, respectively, and/or in collecting receptacles arranged at a distance to the not laser irradiated flow path and flight path of the fluid stream, respectively, wherein the laser irradiation of sections of the fluid stream results in the deflection of these sections of the fluid stream and these move at a spacing from the flow path or flight path of the non-laser irradiated fluid stream, respectively.

In the first embodiment of the invention the laser radiation of the sorting laser has a wavelength which is absorbed by the fluid, such that the laser irradiated section of the fluid stream is heated in a region, especially in the laser irradiated surface section, especially is vapourized, and this section of the fluid stream is accelerated and deflected into the direction opposite of the laser irradiation, respectively. If the fluid is water, preferred wavelengths emitted by the sorting laser are in the range of <350 nm, especially <200 nm or in the range of 1.5 to 6.45 µm, especially of 2 to 3 µm.

In the second embodiment the laser radiation of the sorting laser is focused very narrowly on the surface of the fluid stream, e.g. by optical elements arranged in its beam path and having a numerical aperture in the range from 0.2 to 1.4, especially NA=0.4 to 1.0, are directed onto the fluid. Therein, the focusing of the laser radiation onto the surface of the fluid stream, especially independently from the wavelength of the laser radiation, induces a photodisruption at the fluid surface by nonlinear multiphoton absorption which generates a local superficial evaporation of the fluid and thereby a deflection of the irradiated section of the fluid. The fluid sections separated from the non-irradiated fluid sections by deflection are then caught and collected in separate receptacles, respectively.

Preferred wavelengths are 0.193; 0.222; 0.229; 0.238; 0.244; 0.248; 0.250; 0.257; 0.264; 0.284; 0.308; 0.337; 0.351; 0.364 µm, 1.3-1.8 µm, especially 1.32; 1.35; 1.3686; 1.3772; 1.444; 1.355; 1.45; 1.53; 1.54; 1.5406; 1.5413; 1.5421; 1.5436; 1.5437; 1.5469; 1.5477; 1.5489; 1.55; 1.553; 1.5553; 1.5586; 1.56; 1.5606; 1.665 µm, as well as 1.8-2.7 µm, especially 1.9708; 2.088; 2.123; 2.293 µm, as well as 2.7-4.5 µm, especially 2.791; 2.8; 3.5; 3.8 µm, as well as 4.5, −5.4 µm, especially 4.65; 4.42; 4.48; 4.86; 4.87; 5.25 µm, as well as 5.4-6.5 µm, especially 5.45; 6.13; 6.29 µm, as well as a 6.5-11.5, especially 7.43; 7.62; 7.85; 7.87; 10.09; 10.6 µm.

In both embodiments of the invention the sorting laser is disposed to generate an essentially exclusively superficial heating, especially up to the superficial vapourization of fluid sections. It has been found that thereby no heating within a fluid, especially within an aqueous liquid, is generated which damages biological cells contained therein. This was shown inter alia on human immune cells and on non-human spermatozoa that were singled in an aqueous droplet stream.

In a development the laser that is preferably additionally directed onto the fluid stream is disposed to emit laser radiation which is not in the region of the absorption of the fluid and is directed onto the fluid without optical elements having a numeral aperture of approximately 0.2-1.4, but which radiation can pass through the fluid essentially without absorption, but is absorbed by particles. In this embodiment, particles are heated by the laser irradiation which e.g. for biological cells leads to an inactivation. Preferably, such a laser in this embodiment has a wavelength of approximately 680-1600 nm, e.g. from approximately 680-1100 nm, especially preferred 1041 nm.

Preferably, the radiation of the sorting laser is divided into a first and a second optical path which are directed from different directions onto the same or onto different sections of the fluid stream. For sorting of particles within the fluid stream the laser radiation in the first and second optical path independently from one another is directed onto the fluid stream, each controlled by a control unit. In this manner, sections of the fluid stream arranged in spaced positions independently from one another can be deflected into two different directions and heated, respectively, simultaneously or successively, as described with reference to the first and second embodiments, respectively.

Preferably, the device has a nozzle by which a liquid sheath stream is generated in the core stream of which the particles are spaced axially to the sheath stream, in order to space the particles by the sheath stream from its surface, so that the heating of the surface of this fluid stream does not impair the particles. Preferably, the nozzle is disposed to orient asymmetrical particles, e.g. spermatozoa, into a common plane, e.g. by hydrodynamically effective surfaces shaping the sheath stream. In the alternative or in addition, downstream of an inlet opening of a carrier fluid containing the particles and e.g. forming a core stream within the sheath stream the device can have an optical orienting unit which e.g. is formed by parallel laser beams like an optical and holographic trap, respectively. The device therefore preferably has a laser source emitting at least one, preferably at least two, preferably 4 to 20 parallel laser beams running through the carrier fluid and through the core stream within the sheath stream, respectively. In this embodiment, the nozzle and optionally a conduit or an outlet opening for formation of the core stream, respectively, can have completely circular cross-sections up to their respective outlet opening, so that within the nozzle and within the conduit for the core stream no hydrodynamic orienting of the particles occurs.

The preferred orienting unit according to the invention is directed e.g. onto a section of the fluid stream downstream of the nozzle opening, so that the laser beams forming an optical and holographic trap, respectively, are arranged and directed through a section of the fluid stream, respectively. This trap can e.g. be formed by laser beams having a wavelength in the range of 600-2000 nm.

Preferably, in the method for sorting a dye or a dye conjugate specific for a property of particles, especially a fluorescence dye and a fluorescence dye conjugate, respectively, is added, which specifically labels a portion of the particles.

In a preferred method cells are sorted and the dye conjugate has a specific binding portion, for example an antibody or a binding portion of a natural or synthetic antibody containing a paratope and a dye portion, especially a fluorescence dye. For identification of particles having a specific nucleic acid sequence the dye conjugate can have a specific nucleic acid sequence, especially a nucleic acid sequence specific for a single nucleotide mutation (SNP) or for a sex chromosome.

In the alternative to or in addition to a fluorescence dye a dye conjugate can have a nanoparticle, preferably a nanoparticle in metallic form, especially selected from the group comprising gold, silver, titanium, platinum, iridium, tantalum, iron, nickel, cobalt and copper and mixtures thereof, especially iron-nickel alloys and cobalt-samarium alloys, or in the form of a metal oxide, especially selected from the group comprising oxides of titanium, zinc and iron, especially ferromagnetic metal oxides.

It has been found that in the sorting method for particles carried out by the device also at high volume flow rates and at high sorting rates, respectively, a high sorting purity of a separated fraction corresponding to the detected signal is obtainable, e.g. in comparison to the sorting method according to U.S. Pat. No. 5,135,759 a higher yield and higher sorting purity of a fraction of spermatozoa produced in correspondence to a detected signal, especially for sex-chromosome specific sorting using staining of the total DNA with Hoechst bisbenzimide H 33342, at identical resolution of the detection.

Alternatively, the optical signal used for triggering of the sorting laser can be generated by a dye specific for cell organelles or for the cell surface, e.g. by a lectin or by a DNA specific dye.

Furthermore, spermatozoa fractions produced by the method according to the invention have reduced damages and a higher motility and fertility, especially have significantly reduced damages in comparison to fractions produced by known sorting methods, e.g. at the mitochondria containing sperm middle part. Sperm fractions produced by a method according to the invention therefore e.g. have a motility, measured after an incubation at 38° for 6 h in aqueous medium as unsorted sperms have. Furthermore, sperms fractionated by a method according to the invention preferably have essentially no acrosome damages as is detectable for example by analysis with propidium iodide and/or PSA (pisum sativum agglutinin). Morphological alterations, too, preferably are reduced significantly in spermatozoa fractions sorted according to the invention in comparison to conventionally produced fractions, especially at the same sorting rate.

Accordingly, the invention also relates to cell fractions separated from a mixed cell population, especially sex-chromosome specifically sorted spermatozoa. Such fractions in comparison to conventionally produced fractions are characterized by significantly reduced acrosome damages, especially by a significantly reduced proportion of acrosome damages, which for example are detectable by reaction with propidium iodide and/or PSA, as well as by a significantly reduced proportion of morphological alterations in comparison to the unsorted cell population. Particularly preferred, the proportion of cells, especially of spermatozoa in the fraction produced according to the invention, is less than 20%, especially less than 10% above the proportion of these damages in an aliquot of the unsorted cell population.

Further preferred, the fractions of spermatozoa produced according to the invention have an increased viability which is lower by about less than 20%, preferably by about less than 10% than that of an aliquot of the unsorted cell population, measured under the same conditions as the motility by means of CASA. Accordingly, sperm preparations produced according to the invention, especially sex-chromosome specifically sorted spermatozoa clearly differ from fractions produced by a conventional sorting method. The differences are particularly clear in comparison to spermatozoa sorted according to the method of U.S. Pat. No. 5,125,759 in Tris buffer, e.g. by an essentially increased proportion of motile sperms in the preparations produced by a method according to the invention. E.g., preparations produced according to the invention after approximately 6 h of incubation at 37° in Tris buffer show a proportion of motile spermatozoa from at least 55% to at least 90% of the motility of unsorted sperms of an aliquot, whereas in fractions sorted according to the method of U.S. Pat. No. 5,125,759 the motility after the same incubation had dropped to approximately 10%, each measured automatically by means of CASA. Correspondingly, sperm preparations according to the invention, which are to at least 90 to 95% sex-chromosome specifically pure Y-chromosome containing or X-chromosome containing are characterized by a proportion of motile cells of at least 55% to at least 90% after an incubation at 37° for 6 h in Tris buffer. The motility each time is determined automatically with CASA.

Spermatozoa fractions produced according to the invention preferably in addition to the high proportion of motile spermatozoa have an intact membrane and an intact acrosome at a proportion of at least 80% to at least 90% of the sorted spermatozoa, especially of sex-chromosome specific sorted spermatozoa.

Further preferred, cell fractions produced by specific deflection of a proportion of the cells according to the invention, especially sex-chromosome specifically spermatozoa sorted into fractions, have a proportion of structurally altered and damaged cells, respectively, which does significantly not differ from the proportion of structurally altered and damaged cells in the original cell population, respectively, and which especially is equally high to the proportion of structurally altered and damaged cells in the original cell population, respectively. Particularly preferred, the structural alteration and damage, respectively, is an alteration of the mitochondria, which is visible e.g. electron-microscopically, and/or for spermatozoa an alteration of the sperm middle part which is visible e.g. electron-microscopically. Accordingly, cell fractions, especially spermatozoa fractions, e.g. sex-chromosome specifically sorted sperm fractions, sorted by making single by deflection of cells in the fluid stream according to the invention have structural alterations and damages, respectively, e.g. alterations of the mitochondrial structure, as those the cells have that are not treated according to the invention.

Therefore, the invention also relates to preparations of living isolated cells, with the exception of human gametes, stemming from a mixed cell population and being homogeneous in at least one property and the mitochondria of which have a natural structure and have no higher proportion of impaired mitochondria than the specific cells of the starting population, respectively. The structure preferably is determined electron-microscopically, for spermatozoa alternatively or additionally also as their motility, e.g. by means of CASA.

These properties of the spermatozoa preparations produced according to the invention can be generated using fluids having no content of immobilization means, so that these properties also apply to the sex-chromosome specifically sorted sperm preparations produced according to the invention which were not contacted with immobilization agents and do not contain immobilization agents, especially for sex-chromosome specifically sorted sperm preparations containing no fluoride.

The device preferably is disposed for the laser irradiation of particles in the fluid stream having a rate of 500 particles/s to 6000 particles/s so that upon fractionation by means of laser irradiation having a wavelength absorbable by the fluid, the sorting rate for the particles deflected by means of laser irradiation corresponds to the specific proportion of 500 particles/s to 6000 particles/s, and upon laser irradiation having a wavelength not absorbable by the fluid, the treatment rate corresponds to the specific proportion of 500 particles/s to 6000 particles/s, respectively. Preferably, the device and the method are disposed for detecting the fluid stream at a recognition rate of 60,000 to 70,000/s. The method according to the invention allows higher sorting rates and at identical sorting rates has a higher yield than the deflection of charged droplets in the electric field, because a repolarization of the droplet stream is not necessary, as it occurs upon application of an electrical charge to the droplet stream tearing off. Therefore, in the method according to the invention the selection of singled particles can occur, without the neighbouring particles being influenced by the selection by means of laser irradiation. In contrast to that, upon deflection in the electric field at usual passage rates of up to 2,500 particles/s 3 to 5 subsequent fluid droplets are subjected to the same charge and therefore are sorted into the same fraction independently from the particle.

DETAILED DESCRIPTION OF THE INVENTION

Figure 2:
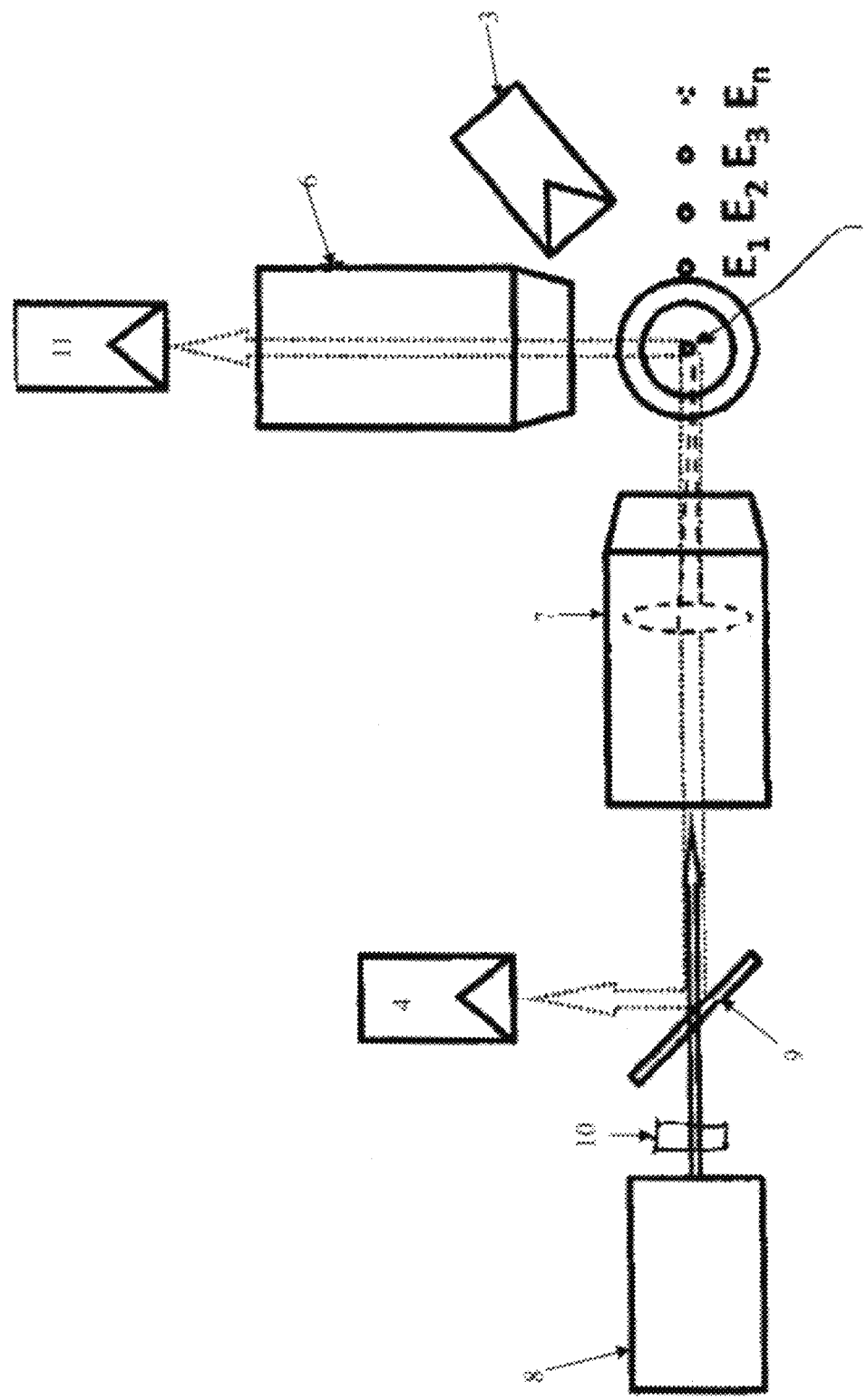
Figure 3:
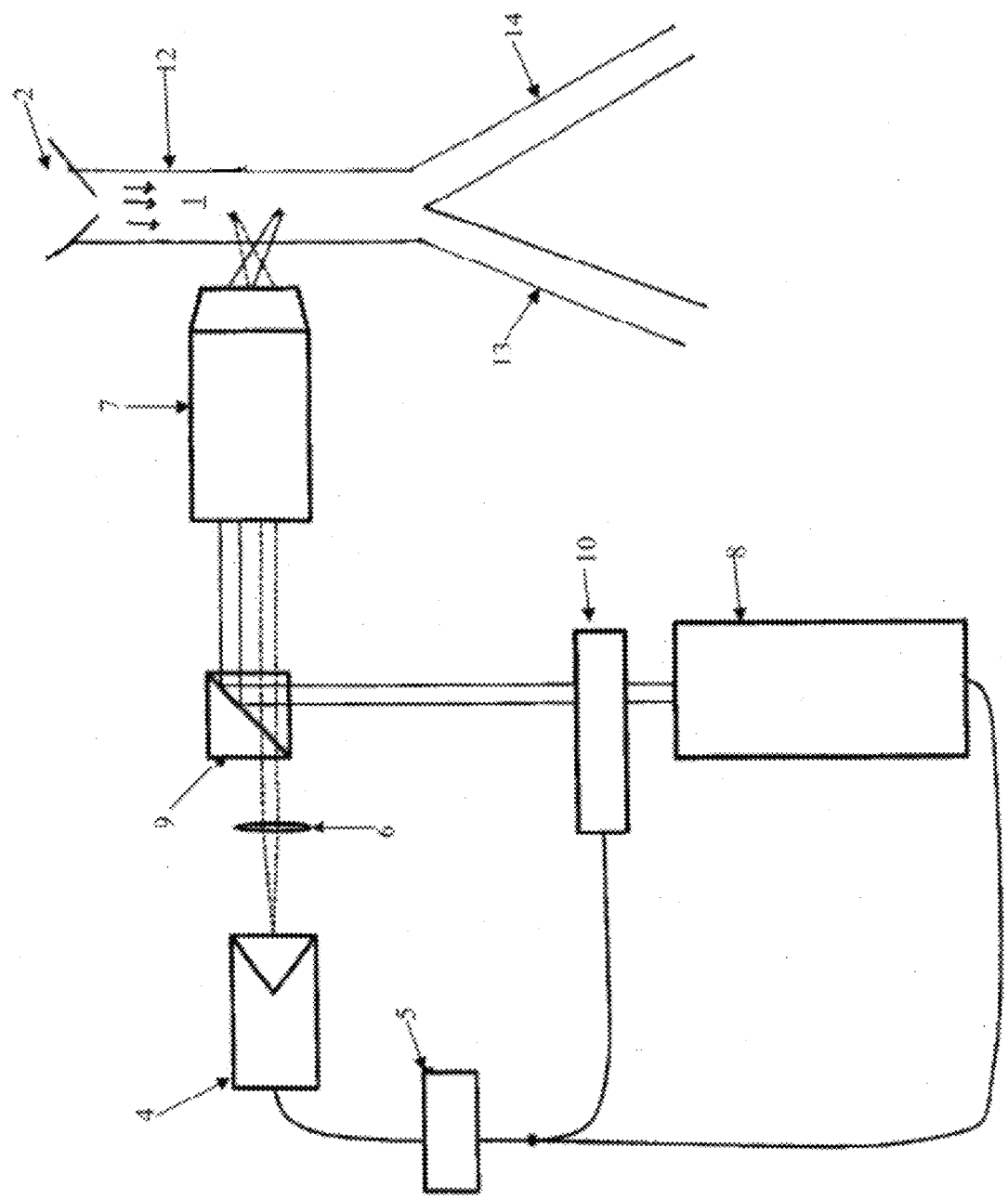
Figure 4:
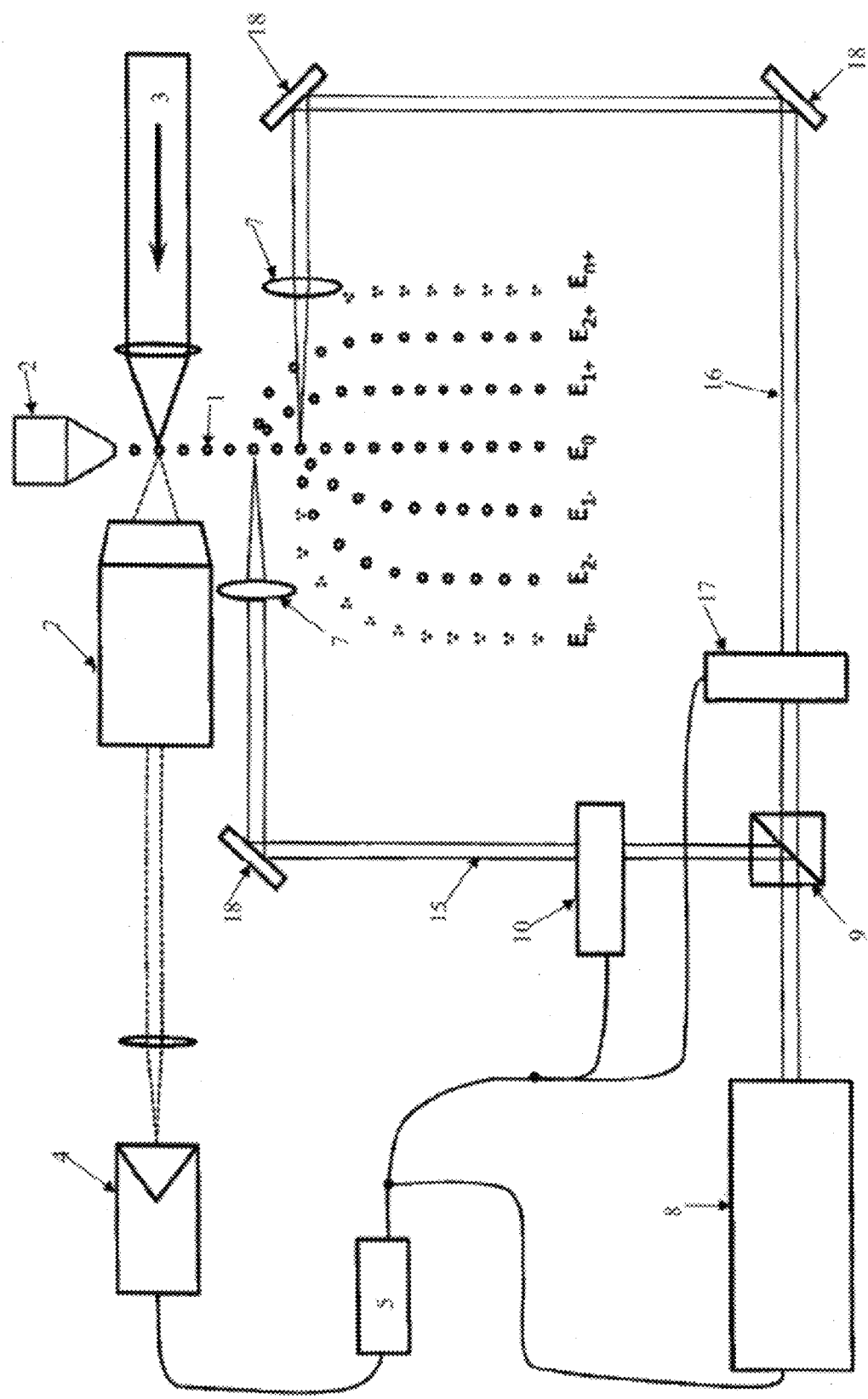
Figure 5:
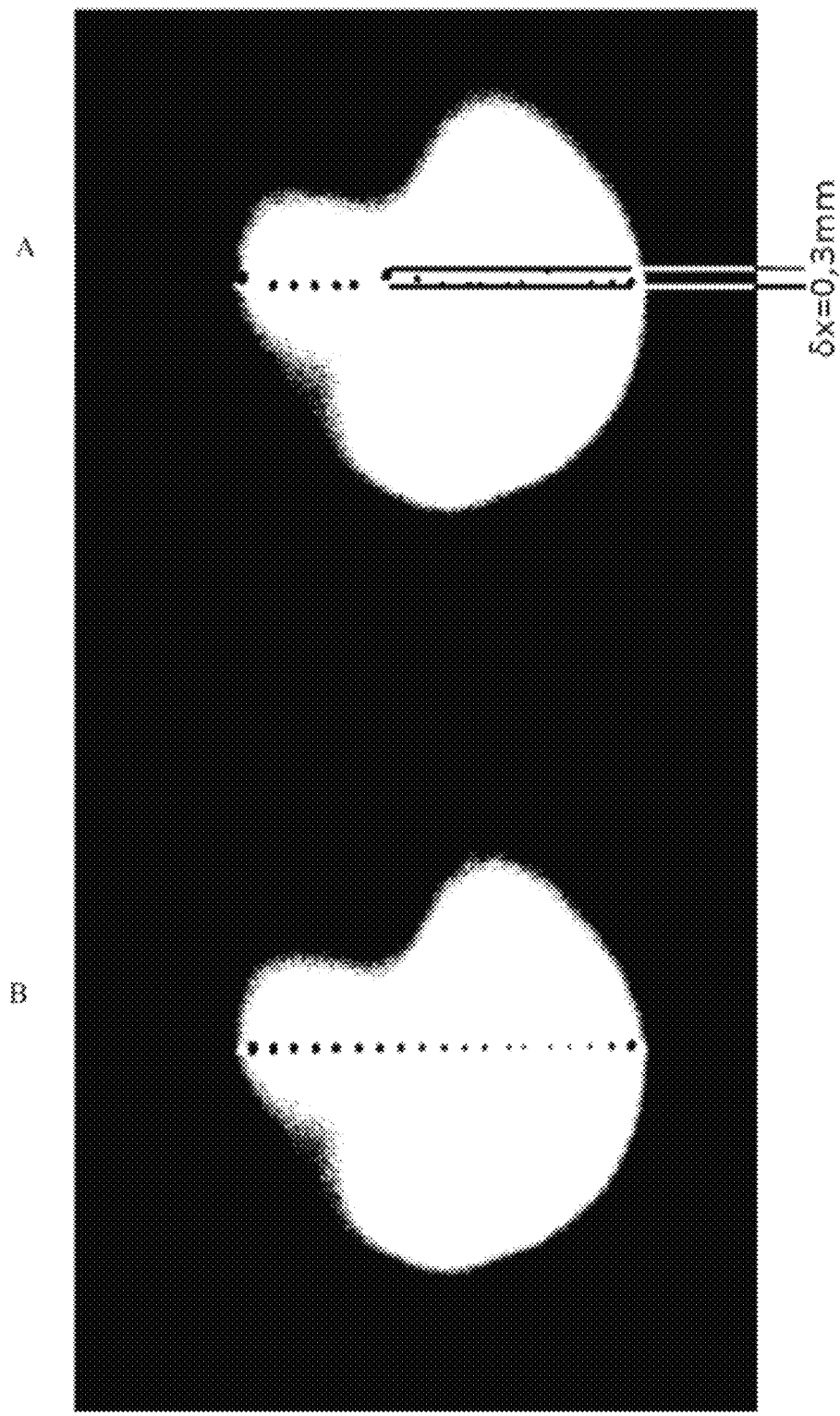
Figure 6:
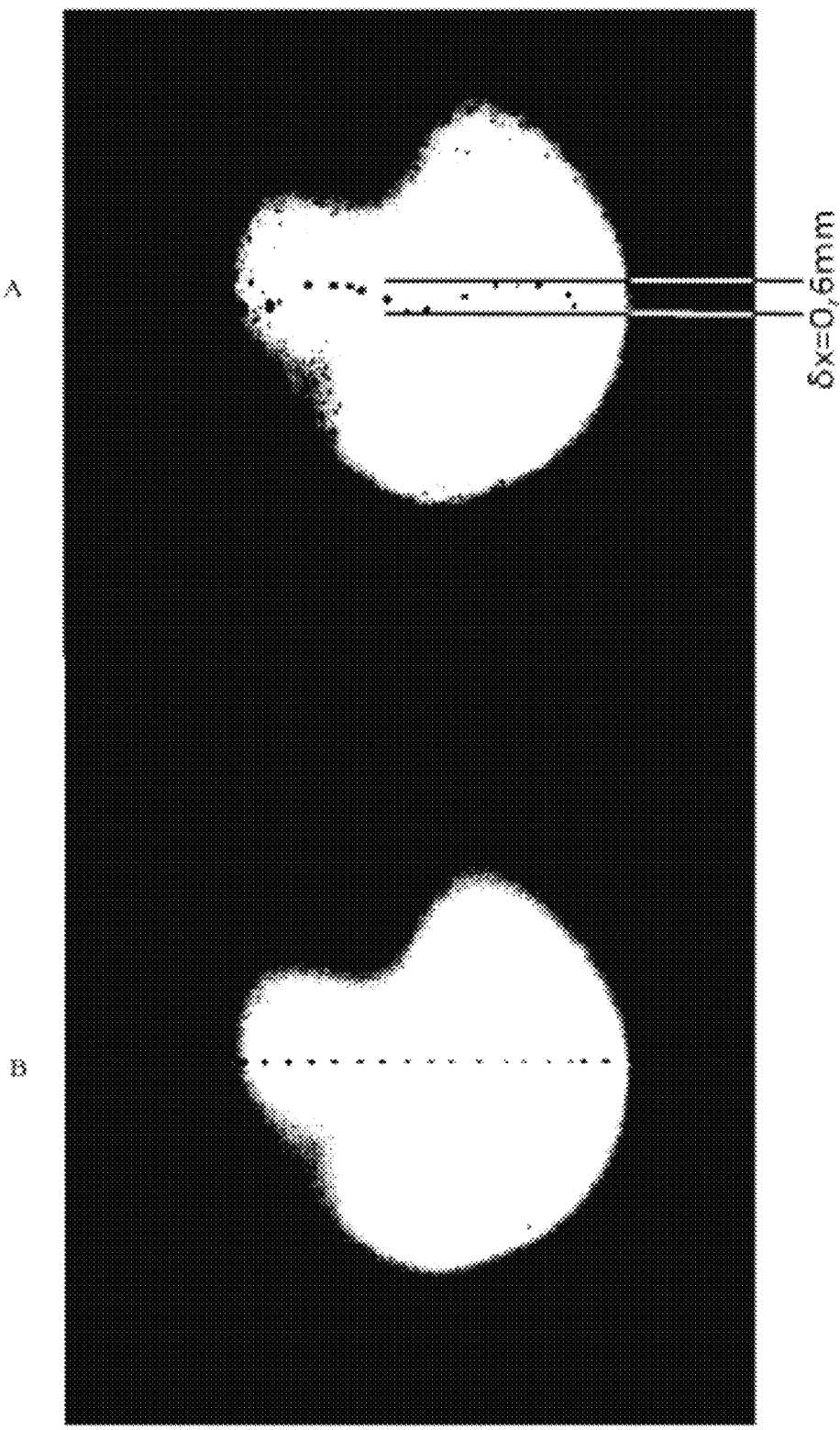
Figure 7:
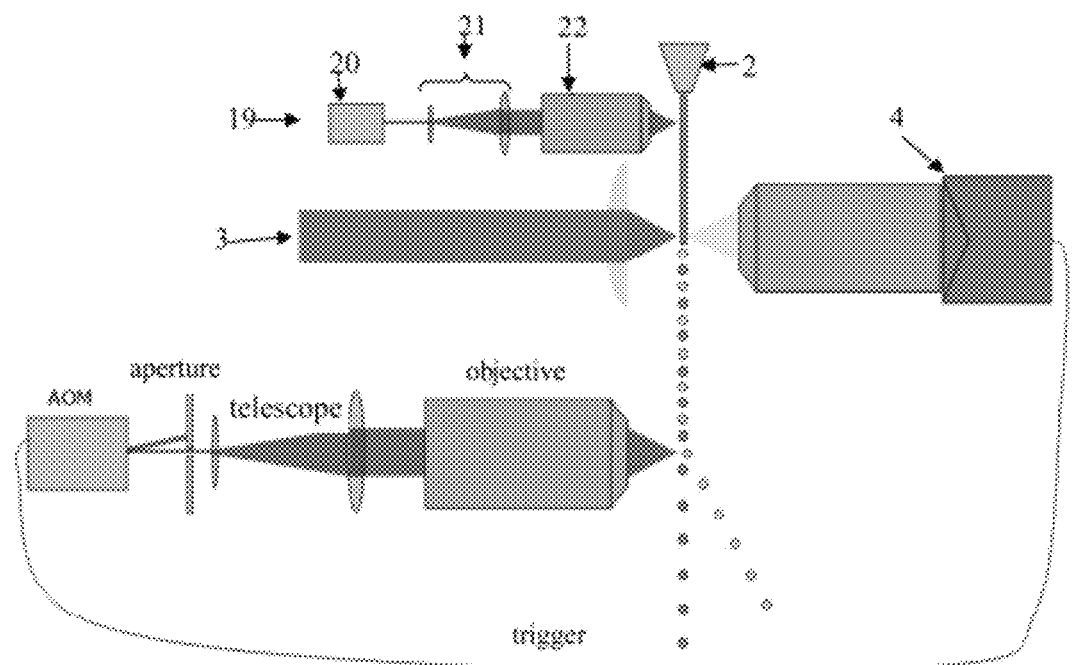

The invention is now described in greater detail by way of examples with reference to the Figures in which FIG. 1 shows a schematic view of a device according to the invention, FIG. 2 shows a view of the device of FIG. 1 rotated by 90°, FIG. 3 shows an alternative embodiment of the device according to the invention, FIG. 4 shows an embodiment of the invention having a division of the laser radiation of the sorting laser into two partial paths, FIG. 5 shows a fluid stream in the form of droplets, under A) without laser irradiation by the sorting laser, and under B) the deflection of droplets by irradiation with the sorting laser, FIG. 6 shows under A) a fluid stream in the form of a droplet stream without laser irradiation by the sorting laser, and under B) the deflection of droplets by irradiation with the sorting laser at increased laser power than used in FIG. 5, and FIG. 7 shows a schematic view of a device according to the invention having an orienting unit forming an optical trap in the fluid stream.

In the Figures, the same reference numerals are used for functionally equal elements. The schematic structure of a device according to the invention is shown in FIG. 1. A fluid stream 1, present in the form of liquid droplets, is generated by exiting a fluid through a nozzle 2. The fluid stream can have the particles in a sheath liquid, and correspondingly, the nozzle 2 preferably in its inner volume has a supply pipe for particles, the outlet opening of which is arranged ahead of the opening of the nozzle 1, whereas a second supply pipe for sheath liquid ends in the inner volume of the nozzle 1. Particularly preferred, the nozzle 1 in its inner volume has a vibrational means, preferably having a vibrational surface approximately in parallel and at a distance to the cross-sectional surface of its nozzle opening, in order to impinge mechanical oscillations in parallel to the flow direction from the nozzle on exiting fluid. Accordingly, it is preferred that the fluid stream is a liquid stream which by impingement mechanical vibrations within the nozzle 1 on the liquid is induced to formation of a droplet stream, wherein the particles are contained in the liquid, preferably are singled in sections of the liquid stream, each section forming individual droplets upon droplet formation.

An irradiation means 3 is directed against the fluid stream 1 and preferably focused on the fluid stream 1. The irradiation means 3 serves for excitation of a dye with which particles were contacted, especially for excitation of the fluorescence dye by which at least a component of a particle was specifically labelled.

In a distance to the fluid stream 1 a detector 4, especially an optical detector or photodetector is arranged which detects the radiation emitted by the fluid stream 1, especially fluorescence, and generates and transmits a measuring signal to a control unit 5 connected to it. The detector 4 preferably is arranged such that radiation emitted by the fluid stream 1 and/or by the particle reaches the detector 4 via a beam path in which at least one collimating lens 6 is arranged. Particularly preferred, a focusing means 7 is arranged in the beam path running from the fluid stream 1 to the detector 4 through which optionally also the beam path of the sorting laser 8 is guided. For separation of the beam paths of the laser radiation of the sorting laser 8 and of the detector 4, respectively, by the focusing means 7, these are coupled into the focusing means 7 at a distance and/or at an angle to each other. Preferably, the focusing means is a microscope objective. For separation of the beam paths of the sorting laser 8 and to the detector 4, respectively, in this case a beam splitter 9 is arranged in the section in which the beam paths of the sorting laser 8 and of the detector 4 run next to each other, especially in parallel to each other, into the focusing means 7. Thereby, the beam splitter 9 reflects the laser radiation of the sorting laser 8 in an angle, e.g. of 90°, into the focusing means 7, whereas the beam splitter 9 passes the radiation emitted by the fluid stream 1, generated by the irradiation of the irradiation means 3 from the focusing means 7 to the detector 4.

The laser radiation of the sorting laser 8 preferably is controlled by an optical switch 10 controlled by the control unit 5 such that the laser radiation under the control of the optical switch 10 by the focusing means 7 is directed onto a section of the fluid stream 1. Apart from the optical switch 10, the sorting laser 8 itself can be connected to the control unit 5 such that the control unit 5 can also control the radiation power of the sorting laser 8 in dependence from the detection signal received by the detector 4. Accordingly, the control unit 5 can also be denoted as a tripping unit and triggering unit, respectively, since it trips the optical switch 10 and/or the sorting laser 8 and therefore trips the laser radiation affecting the fluid stream 1. Preferably, the control unit has a delaying unit and correspondingly can also be denoted as trigger-delay unit.

Laser radiation generated by the sorting laser 8 under the control of the control unit 5 upon transparency of the optical switch 10 is coupled by the beam splitter 9 into the focusing means 7 and is directed onto a second position of a section of the fluid stream 1 downstream of the first position of a section of the fluid stream 1 for which under the influence of the irradiation means 3 the detector 4 has generated and transmitted a measuring signal to the control unit 5. Due to the arrangement of the second position of the section of the fluid stream 1 downstream and temporally after the first position of the section of the fluid stream 1 for which the detector 4 produces a measuring signal, respectively, laser radiation generated by the sorting laser 8 in the second position upon control with delay of the laser irradiation to the measuring signal due to the movement of the fluid stream 1 affects the originally measured section of the fluid stream 1, and correspondingly the same section of the fluid stream 1 for which a measuring signal was generated by the detector 4 in the first position.

The influence of the laser radiation onto the fluid stream 1 according to the first embodiment leads to heating of the fluid near the surface on one side depending on the wavelength of the laser radiation and, due to the expansion, for example evaporation of a portion of a liquid droplet, this section of the fluid stream is deflected, as is schematically shown by the partial fluid streams deflected to the right of the linear orientation of the fluid stream 1. Therein, the degree of the deflection depends on the input of energy by the laser irradiation so that the degree of deflection of sections of the fluid stream caused by the laser irradiation results in the division of the sections of the fluid irradiated by laser from the sections not irradiated by laser.

Collecting receptacles for collecting the non-deflected sections of the fluid stream and the deflected sections of the fluid stream can each be arranged at a distance to one another corresponding to the flow path of the fluid stream not irradiated by laser ($E_0$), and corresponding to the deflection of sections of the fluid stream irradiated by laser ($E1$, $E2$, $En$, with increasing energy of the laser irradiation), respectively.

With the disposition of the sorting laser 8 such that its radiation had a pulse energy of 1.8 μJ, and 3.5 μJ, respectively, and was focused onto a surface section of the fluid stream 1, using a fluid stream 1 streaming perpendicularly downwards (with up to 60,000 droplets/s, 6 m/s) a deflection of droplets by 200 μm and 400 μm on a path length of 3 cm, respectively, could be achieved. The deflection occurred into the direction opposite the focused laser beam. With a flow path and falling path, respectively, of 15 cm subsequent to the region irradiated by the sorting laser, from this deflection already a spacing of 1.5 mm to the vertical results. This result shows that by the superficially produced photodisruption a repulsion was generated by the evaporation of the fluid stream that was superficial only, which is sufficient for the targeted guidance of the droplets into at least a flow path and falling path, respectively, spaced from the non-influenced flow path and falling path, respectively. The wavelength of the radiation emitted by the sorting laser was selected as 2.94 μm as example for the first embodiment, and as 1041 nm with a numerical aperture of the optical elements arranged in the beam of 0.4 as an example for the second embodiment, in which only the focusing of the laser radiation on the surface of the fluid stream, especially independently from the wavelength, results in the generation of only a superficial heating of the fluid.

FIG. 2 shows the device of FIG. 1 rotated by 90° in a variant, which in addition to a detector 4 contains a second detector 11 which detects radiation at an angle to the beam path which is guided to the (first) detector 4 by means of the objective 7. Such a second detector 11, preferably having a collimating lens 6, for example in the form of a microscope objective in its beam path, can serve for detection of a second property of the fluid stream and the particles contained therein, respectively.

An irradiation means 3 serves for excitation of fluorescence. By means of a beam splitter 9, preferably a dichroitic beam splitter 9, the sorting laser 8 in accordance to FIG. 1 is coupled into the focusing means 7 which directs the laser radiation onto the fluid stream 1 exiting from the nozzle 2. The laser irradiation deflects sections of the fluid stream into the opposite direction and generates partial fluid streams $E1$, $E2$, $E3$ to $En$, if the laser radiation has a wavelength which is absorbed by the fluid stream 1, or the laser radiation heats particles within the fluid stream 1 without causing a significant deflection of the fluid stream 1 when the laser radiation has a wavelength for which the fluid stream 1 is optically transparent and which is absorbed by the particle.

In the focusing means 7, a collimating lens is schematically shown which is to focus the laser radiation on the fluid stream 1.

FIG. 3 shows an alternative embodiment in which the fluid stream 1 flows in a laminar way in a flow channel 12. Here, the nozzle 2 can be arranged in the form of an inlet opening at an inlet end of the flow channel 12. Due to the formation of the fluid stream 1 as a laminar fluid stream 1, the detection of fluorescence according to the invention which is measured in a detector 4 from a label of a particle after irradiation of excitation radiation by an irradiation means 3, and a section of the flow channel 12 arranged downstream in the flow direction of the fluid stream 1 can be irradiated with laser radiation of the sorting laser 8, so that upon delay of the laser irradiation in correspondence to the velocity of the fluid stream 1, the same section of the fluid stream 1 can be exposed again to a laser radiation for which the detector 4 has generated and transmitted a measuring signal to the control unit 5.

According to the first embodiment of the invention it is provided that the particle contained in this section of the fluid stream is deflected by irradiation of laser radiation having a wavelength which is absorbed by the fluid stream. In this embodiment, the flow channel 12 at a branching transforms into two or more branching channels 13, 14, such that particles are deflected into a branching channel 14 in correspondence to the deflection by laser irradiation of the sorting laser 8 of a portion of the fluid stream 1, whereas particles not deflected by laser irradiation are transported into the branching channel 13 with the other partial stream of the fluid stream 1.

For the second embodiment, the sorting laser 8 is disposed to emit laser radiation having a wavelength for which the fluid stream 1 is optically transparent, but which is absorbed by labelled particles. Correspondingly, in this embodiment, labelled particles are heated or non-labelled particles are heated, respectively, in order to inactivate these in a targeted manner, for example in the case of biological cells, especially spermatozoa. Since in the second embodiment a deflection of the particles does not occur in significant extent, a division of the fluid stream 1 is not necessary.

FIG. 4 shows a development of the embodiments of the invention in which the laser radiation generated by the sorting laser 8 is divided into a first sectional beam 15 and into a second sectional beam 16 at a beam splitter 9, wherein in the first sectional beam 15 a (first) optical switch 10 and in the second sectional beam a second optical switch 17 is arranged, each of which is controlled independently from the other one by the control unit 5 to which they are connected. First and second sectional beams 15, 16 are directed onto the fluid stream 1 each, for example by means of mirrors 18, and preferably the second sectional beam 16 is focused by two mirrors 18 each arranged in 45° to the sectional beam 16 onto a section of the fluid stream 1, preferably by means of a focusing means 7. The first sectional beam 15 is directed onto the fluid stream 1, preferably by means of a mirror 18, and also preferably is focused by a focusing means 7. Particularly preferred, the first sectional beam 15 is focused on the fluid stream 1 at an angle of 90°-180°, especially 180° to the second sectional beam 16, such that in correspondence to the first embodiment, both the first sectional beam 15 and the second sectional beam 16 independently from one another irradiate the same or spaced sections of the fluid stream 1. According to the first embodiment it is preferred that the first sectional beam 15 and the second sectional beam 16 are focused onto the fluid stream 1 at a spacing from one another and the sorting laser 8 emits laser radiation at a wavelength which is absorbed by the fluid stream 1. In this manner, sections of the fluid stream 1 can be deflected into different directions by irradiation of the first and second sectional beams 15, 16, respectively, in order to establish the precision of the sorting by spacing the sections of the fluid stream 1 corresponding to the detected measuring signal from one another, for example as depicted in FIG. 4, are deflected into fractions $E_{1+}$, $E_{2+}$, $E_{n+}$ by the irradiation with the first sectional beam 15, and in the opposite direction are deflected into the fractions $E_{1-}$, $E_{2-}$, $E_{n-}$ by irradiation by the second sectional beam 16. Non-irradiated sections of the fluid stream 1 are not deflected and form the fraction $E_0$.

FIG. 5 shows an ultrashort-time photograph of a fluid stream of water, under A) without laser irradiation, and under B) upon targeted irradiation of individual droplets representing the sections of the fluid stream, at laser irradiation having a wavelength of 1041 nm. The energy applied onto a droplet of the fluid stream was approximately 1.8 µJ. As becomes clear from FIG. 5 B), sections of the fluid stream are deflected into the direction opposite to the laser irradiation by the irradiation with laser radiation having a wavelength which is absorbed by the fluid stream. The deflection in this case was approximately 0.3 mm immediately following application of the laser radiation.

FIG. 6 shows photographic pictures exposed for an ultrashort time corresponding to FIG. 5, but with a CW sorting laser which at 1041 nm radiated at a power of 350 mW and in the beam path of which an optical switch was arranged, such that the energy radiated onto a fluid droplet was 3.54 µJ. While FIG. 6A shows that without influence of laser radiation the fluid stream runs in a linear way, FIG. 6 B shows that the irradiated laser radiation results in a deflection of the liquid droplets by approximately 0.6 mm As an example for particles and biological cells, respectively, bull spermatozoa were used which after collecting were obtained by known methods and diluted in Tris buffer and were stained with Hoechst bisbenzimide H 33342 at room temperature. After the staining the spermatozoa were sorted in a FACS device which was designed according to the description of U.S. Pat. No. 5,135,759 with the exception of the sorting means. This modified device schematically corresponded to FIG. 1 and had a sorting laser (1041 nm, 350 mW) which was directed onto a section of the droplet stream below the nozzle by means of a microscope objective as focusing means. An optical switch arranged in the beam path of the sorting laser was controlled by a control unit having a trigger-delay function which was controlled on the basis of the measuring signals which were received by a first optical detector which detected the intensity of the fluorescence signal of the DNA specific Hoechst dye, and a second optical detector which detected radiation in perpendicular to the radiation measured by the first detector and which gave a signal for the orientation of the spermatozoa after exiting from the nozzle. The control unit was set such that only for spermatozoa which were oriented with their flat site in perpendicular to the beam path of the first detector a control signal was generated for transmission by the optical switch and in addition, such a control signal was generated only for X-chromosome bearing spermatozoa so that laser radiation of the sorting laser was radiated onto the fluid stream only for correctly oriented X-chromosome bearing spermatozoa.

For consideration of the temporal delay between the detection of the measuring signals by the first and second detectors to the irradiation of laser radiation by means of transmission by the optical switch which also considered the calculation time of the control unit, the laser radiation was directed onto a second position of a section of the fluid stream at a further distance from the nozzle than the first position in which for the same section of the fluid stream the fluorescence was measured by means of the first and second detectors.

An analysis of spermatozoa at a sorting rate of 500/s resulted in a purity of the collected fraction of above 90% X-chromosome bearing spermatozoa which were motile to more than 80%. The motility could be detected in an automatic test (CASA, computer assisted sperm analyzer) at incubation at 37° in Tris buffer over a period of time of at least 6 h for at least 50% of the spermatozoa. A control of the integrity of the acrosomes of the sorted fraction revealed that essentially no acrosome damages had occurred. In particular it was determined that the detection with propidium iodide was negative for 85% and the analysis with PSA (PSA conjugate with FITC) was also negative for 90% of the spermatozoa in the sorted fraction, i.e. showed no damages due to destruction of the acrosome membrane.

Upon adjustment of the control unit such that only upon detection of correctly oriented Y-chromosome bearing spermatozoa laser radiation by means of the optical switch was allowed to act on the fluid stream, correspondingly a Y-chromosome bearing spermatozoa fraction could be produced which essentially showed the same cellular properties.

In a comparative test, a flow cytometric device having a sorting unit which generates an electric field between two plates and in which the departing droplet stream is electrically charged according to the detector signal was used for sorting of spermatozoa. In a first batch spermatozoa were singled in sheath liquid (Tris buffer) in a droplet stream of 2500/s and were dropped through the electric field (3000 V) without laser irradiation and without electrical charge of the droplet stream. The droplets were immediately collected on microscope slides and the motility of the sperms was optically determined by means of automatic methods (CASA). For comparison, the motility of an aliquot of the sample that was not treated flow cytometrically was determined and the motility of spermatozoa in droplets identically collected which had passed through the same device in a droplet stream but without electric field. The average motility for the spermatozoa which had passed through the electric field was 13.333, standard deviation (SD) 4.082, SEM 1.667, whereas the spermatozoa which with the exception of the electric field had passed the device identically as well as the aliquot not treated flow cytometrically had an average motility of 67.500, SD 4.183, SEM 1.708. The difference of 54.167, t=22.699 (10 degrees of freedom) with $P \leq 0.001$ is significant (including normality test P=0.055, variance test P=0.670). This comparison shows that solely the electric field of the conventional sorting means for the deflection of cells into separate fractions leads to damaging of cells of resulting in a highly significant reduction of the motility ($P \leq 0.001$). The laser was switched off each time and therefore could have no influence.

In a further comparison bull sperms were sorted according to the method of U.S. Pat. No. 5,125,759 by deflection in correspondence to the DNA content detected in charged liquid droplets in the electric field in Tris buffer, or were deflected according to the method of the invention by means of laser irradiation having a wavelength which caused a superficial evaporation. For comparison, unsorted sperms were used. The analysis by means of CASA shows that immediately after the sorting all collected fractions as well as the unsorted control had a motility of 75%, but subsequent to an incubation in Tris buffer at 38° for 6 h, the electrostatically deflected sperms showed a motility of only approximately 50%, whereas the sperms deflected according to the invention as well as the unsorted sperms showed a motility of approximately 60%. The microscopic analysis of the morphology of 200 sperms each after the incubation for 6 h at 38° revealed lower damages in the sperms sorted according to the invention than in the electrostatically deflected sperms. The results are summarized in the following table:

| Morphologically intact sperms: | | | |
|---|---|---|---|
| | unsorted | electrostatically deflected liquid droplets | liquid droplets deflected by laser beam |
| immediately after sorting | 90.5% | 92.5% | 89% |
| after 6 h, 38° C. | 89% | 81% | 82.5% |
| loss of intact cells | 1.5% | 11.5% | 6.5% |

FIG. 7 shows a device for sorting which is suitable especially for asymmetric cells, e.g. for spermatozoa, having an optical orienting unit 19 that is directed onto a region of the fluid stream 1 between nozzle 2 and the region in which the radiation of the irradiation means 3 and the detector 3 arranged opposite thereto are directed onto the fluid stream. The orienting unit 19 e.g. has an orientation laser 19 which by means of an optical system, e.g. a telescope 21 and an objective 22 is directed onto the fluid stream 1. Alternatively, the optics can have an optically conducting fibre or can consist thereof. Preferably, the orientation laser 20 generates radiation having a wavelength of 600 to 2000 nm, preferably having an arrangement of optical elements suitable for the generation of the photodisruption at the surface of the liquid, which optical elements have a numerical aperture of 0.2 to 1.4. Optionally, the optics can have elements in the beam path dividing the radiation of the alignment laser 20 into two or more parallel sectional beams, e.g. a beam splitter and a reflector directing the sectional beam deflected by the beam splitter onto the fluid stream and in parallel to the sectional beam that passes through the beam splitter.

LIST OF REFERENCE NUMERALS

1 fluid stream
2 nozzle
3 irradiation means
4 detector
5 control unit
6 converging lens
7 focusing means
8 (sorting) laser
9 beam splitter
10 optical switch
11 second detector
12 flow channel
13 branching channel
14 branching channel
15 first sectional path
16 second sectional path
17 second optical switch
18 mirror
19 alignment unit
20 alignment laser
21 telescope
22 objective

The invention claimed is:
1. A device for the selection of particles having a nozzle for the generation of a fluid stream containing particles, an irradiation means directed onto the fluid stream exiting from the nozzle, a detector directed onto the fluid stream and disposed for generation of measuring signals, a control unit, connected to the detector and disposed for receiving detection signals and for generation of control signals for a selection unit, and a selection unit connected to the control unit disposed for receiving the control signals, wherein a plurality of collecting receptacles are positioned to receive fluid sections;

the selection unit has a sorting laser, said sorting laser being directed on the fluid stream and being powered and controlled by the control unit to apply a total energy sufficient to heat the surface of the fluid stream to a superficial vaporization temperature, whereby a section of the fluid stream irradiated by the laser irradiation is accelerated into the direction opposite the laser irradiation and collected in a collecting receptacle designated for a deflected fluid section, while a non-deflected fluid section flows to a second collecting receptacle designated for the non-deflected fluid section.

2. The device according to claim 1, wherein the sorting laser is pulsed.

3. The device according to claim 1, wherein the sorting laser has a wavelength which is absorbable by the fluid stream, and wherein the laser radiation is focused on the surface of the fluid for induction of a photodisruption at the surface of the fluid by nonlinear multiphoton absorption.

4. The device according to claim 1, wherein the sorting laser comprises optical elements having a numerical aperture of 0.2 to 1.4 in the beam path of the laser beam which focus the laser beam on the surface of the fluid stream.

5. The device according to claim 1, wherein the sorting laser is a CW laser in the beam path of which an optical switch controlled by the control unit, is arranged, a CW laser which is capable of modulation or a CW laser having a connected triggering unit.

6. A device according to claim 1, wherein the detector is an optical detector directed onto a first position of the fluid stream and the sorting laser is focused onto a second position of the surface of fluid stream further from the nozzle than the first position.

7. The device according to claim 1, wherein the control unit comprises delay unit disposed for controlling the laser and for delaying the irradiation of the laser radiation onto the fluid stream.

8. The device according to claim 1, comprising focusing means for focusing the laser beam onto the surface of the fluid stream, and wherein the detector is an optical detector in a beam path of the laser beam.

9. The device according to claim 8, further comprising a particle laser focused on the fluid stream controlled by the control unit to generate radiation having a wavelength transparent to the fluid stream, wherein the particle laser has a wavelength and is controlled by the control unit to apply energy to heat the particles to a thermal inactivation temperature.

10. The device according to claim 1, further comprising a beam splitter in the beam path of the sorting laser dividing the laser beam into a first sectional path directed onto the fluid stream and into a second sectional path directed onto the fluid stream, wherein in the first sectional path and/or in the second sectional path at least one mirror is arranged for orienting laser radiation onto the fluid stream.

11. The device according to claim 1, further comprising an alignment laser directed onto the fluid stream between the nozzle and the detector.

12. The device according to claim 1, wherein the nozzle generates a fluid stream of liquid droplets.

13. A method for the selection of particles by formation a fluid stream containing the particles, detecting one property of a particle within the fluid stream, generation of a detection signal specific for the property, generation of a control signal based on the detection signal, controlling a selection unit by means of the control signal, and treating one of the particles in dependence from the control signal, wherein a surface of the fluid stream is irradiated by the selection unit with laser radiation from a sorting laser which in a second position arranged at a greater distance from the nozzle than the first position of the fluid stream in which the property detected is directed onto the fluid stream only superficially, wherein the sorting laser is directed on the fluid stream and is powered and controlled to apply a total energy sufficient to heat the surface of the fluid stream to superficial vaporization temperature whereby a section of the liquid stream irradiated by the laser irradiation is accelerated into the direction opposite the laser irradiation, wherein the non-deflected fluid sections are collected in a collecting receptacle arranged in the flow path of non-deflected fluid sections and deflected fluid sections are collected in a collecting receptacle arranged in the flow path of deflected fluid sections.

14. The method according to claim 13, wherein the sorting laser radiation has a wavelength which is absorbed by the fluid.

15. The method according to claim 13, wherein the sorting laser radiation is focused on the surface of the fluid for induction of a superficial photodisruption is focused on the surface of the fluid.

16. The method according to claim 13, wherein the particles are contacted with a dye or dye conjugate having a binding portion specific for a component of a particle, and the detection signal is generated by detection of the dye.

17. The method according to claim 13, wherein the fluid stream is a stream of liquid droplets.

18. The method according to claim 13, wherein the sorting laser generates beam pulse energies in the range from 1 to 10 $\mu J$.

19. The device according to claim 1, wherein the sorting laser is set to generate beam pulse energies in the range from 1 to 10 $\mu J$.

* * * * *